United States Patent [19]

Sarnoff et al.

[11] Patent Number: 4,484,910
[45] Date of Patent: Nov. 27, 1984

[54] DUAL MODE AUTOMATIC INJECTOR

[75] Inventors: Stanley J. Sarnoff; George B. Calkins, both of Bethesda; Claudio Lopez, Silver Spring, all of Md.

[73] Assignee: Survival Technology, Inc., Bethesda, Md.

[21] Appl. No.: 563,767

[22] Filed: Dec. 21, 1983

[51] Int. Cl.³ .............................................. A61M 5/20
[52] U.S. Cl. ................................... 604/136; 604/134; 604/157
[58] Field of Search ............... 604/136, 134, 135, 138, 604/141, 143, 144, 131, 137, 139, 157, 130; 74/553, 558.5; 16/121

[56] References Cited

U.S. PATENT DOCUMENTS

| 2,832,339 | 4/1958 | Sarnoff | 604/135 |
| 3,320,955 | 5/1967 | Sarnoff | 604/135 |
| 3,712,301 | 1/1973 | Sarnoff | 604/135 |
| 3,797,489 | 4/1974 | Sarnoff | 604/135 |
| 3,882,863 | 5/1975 | Sarnoff | 604/135 |
| 4,031,893 | 6/1977 | Kaplan | 604/135 |
| 4,226,235 | 10/1980 | Sarnoff et al. | |
| 4,316,463 | 2/1982 | Schmitz | 604/135 |
| 4,329,988 | 5/1982 | Sarnoff et al. | |
| 4,394,863 | 7/1983 | Bartner | 604/135 |

Primary Examiner—Stephen C. Pellegrino
Assistant Examiner—Mark Rooney
Attorney, Agent, or Firm—Cushman, Darby & Cushman

[57] ABSTRACT

A dual mode automatic injector having a dual mode safety device for preventing the release of the stressed spring assembly except when it is desired to operate the medicament injecting assembly by the stressed spring assembly. The dual mode safety device comprises a first part including a pin portion disposed in a safety position extending through a central aperture in the rear wall of the housing assembly of the injector in release preventing relation with the stressed spring assembly for removal therefrom in response to a relative rearward movement with respect to the rear wall so as to permit an actuating movement to release the stressed spring assembly. The first part includes an automatic removal portion fixed to the rearward end of the pin portion. The automatic removal portion is of a size greater than the pin portion but less than the rear wall so as to present a forwardly facing surface spaced rearwardly from the rear wall operable to be engaged by a holding member while a moving member is moved forwardly into engagement with the rear wall to provide both a relative rearward removal movement for the pin portion and an actuating movement for the stressed spring assembly. The dual mode safety device also includes a separate second part and a connection between the first and second parts for (1) enabling the second part to be connected with the first part while the pin portion of the latter is in its safety position in a manual mode position wherein the first part is in rearward motion transmitting relation to the second part and (2) enabling the second part to be removed from the manual position while the pin portion of the first part is retained in its safety position. The second part includes a cap portion of a size and shape to be conveniently manually grasped by a user and moved rearwardly with respect to the housing assembly in order to effect the removal of the pin portion from its safety position when the second part is in its manual mode position.

8 Claims, 5 Drawing Figures

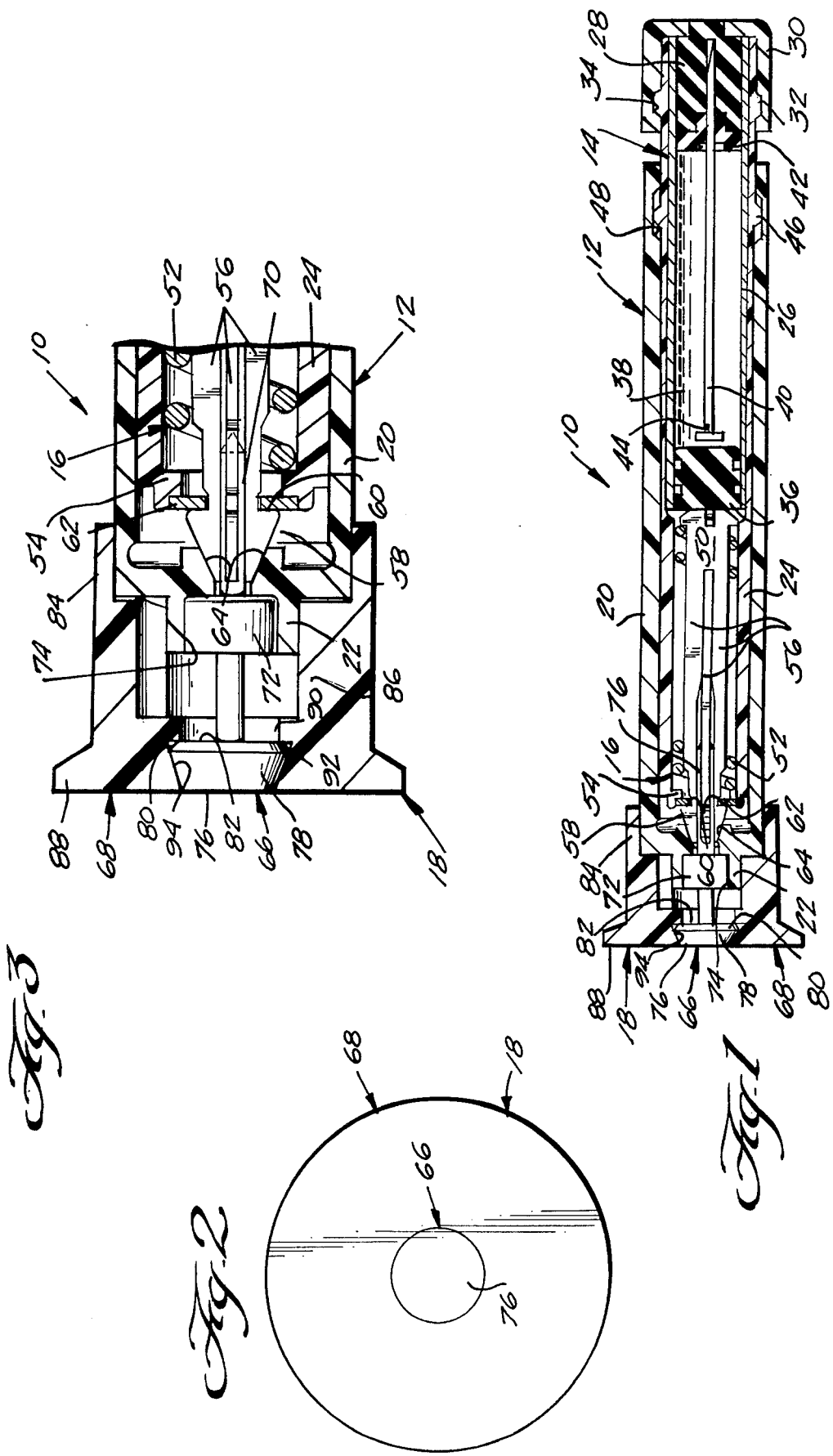

DUAL MODE AUTOMATIC INJECTOR

This invention relates to automatic injectors and, more particularly, to improvements in the safety for an automatic injector which renders the injector suitable to be selectively operable in either one of two different modes of operation.

The type of automatic injector herein contemplated is the type specifically used by military personnel to administer an antidote for nerve gas exposure under chemical warfare conditions. A typical automatic injector currently provided for injecting a dosage of atropine is disclosed in U.S. Pat. No. 2,832,339. A more recent U.S. Pat. No. 4,329,988 discloses more accurately the exact configuration of the currently provided injector. The more recent patent depicts the injector in combination with a second automatic injector containing a relatively larger dosage of pralidoxime chloride and a holder for stably supporting the two separate injectors together and for manually facilitating the sequential actuation thereof. More recently, it has been proposed to replace the holder —separate injectors—combination with a unitized two dosage automatic injector which eliminates the need for sequential manual actuation of two separate automatic injectors and provides for the accomplishment of substantially simultaneous injections in response to a single manual actuation. Unitized plural automatic injectors are disclosed in U.S. Pat. No. 4,226,235. A more recent embodiment is disclosed in commonly assigned U.S. patent application Ser. No. 563,768 filed concurrently herewith and entitled "Plural Dosage Automatic Injector with Improved Safety". In the injector disclosed in the application, the current atropine automatic injector except for its safety is used as a unitary component of the plural dosage injector. Instead of the usual manually removable safety which consists of an exteriorly flanged cap member having a central pin extending axially therefrom there is provided an automatic safety which consists of a pin having an enlarged removal portion on the rearward end thereof. The enlarged removal portion is spaced rearwardly of the centrally apertured rear wall of the outer housing member of the injector and is of a size greater than the pin so as to provide a forwardly facing surface for engaging a fixed abutment. Moreover, its size is less than the rear wall of the housing member so as to permit an actuating member rearward access to the rear wall. The operation of the plural dosage injector is such that the actuating member is moved forwardly through a secondary actuating movement in response to the initial manual actuation of the plural dosage automatic injector. The secondary actuating movement of the actuating member moves the atropine injector forwardly as a unit together with an overfitted forward support cap member. During the initial portion of the secondary actuating movement the automatic safety pin is held against forward movement by the abutment so that at the end of the initial portion of the movement it has been removed from its safety position. Thereafter the forward movement of the forward cap member is arrested so that the further forward movement of the outer housing member by the actuating member positively accomplishes actuation and release of the stressed spring to operate the atropine injecting assembly.

The atropine automatic injector currently being used has a useful life of approximately five years. One of the problems which arises when these injectors are combined with pralidoxime chloride automatic injector components is that the pralidoxime chloride has only a useful life of three years. It is, therefore, desirable to be able to use the atropine injector as a single unit for two years either before or after it is combined with pralidoxime chloride injector components. Moreover, it is important to enable a potential user to simply condition the atropine injector selectively for use in either mode, that is either in a single dosage mode by itself or in the plural dosage mode with the pralidoxime chloride injector components. Finally, it is essential in providing the above capabilities that the safety can at all times be retained in its safety position.

Accordingly, it is an object of the present invention to provide a dual mode automatic injector which will accomplish all of the above noted requirements. In accordance with the principles of the present invention this objective is obtained by providing the injector with a dual mode safety device for preventing the release of the stressed spring assembly except when it is desired to operate the medicament injecting assembly by the stressed spring assembly. The dual mode safety device comprises a first part including a pin portion disposed in a safety position extending through a central aperture in the rear wall of the housing assembly of the injector in release preventing relation with the stressed spring assembly for removal therefrom in response to a relative rearward movement with respect to the rear wall so as to permit an actuating movement to release the stressed spring assembly. The first part includes an automatic removal portion fixed to the rearward end of the pin portion. The automatic removal portion is of a size greater than the pin portion but less than the rear wall so as to present a forwardly facing surface spaced rearwardly from the rear wall operable to be engaged by a holding member while a moving member is moved forwardly into engagement with the rear wall to provide both a relative rearward removal movement for the pin portion and an actuating movement for the releasable means. The dual mode safety device also includes a separate second part and a connection between the first and second parts for (1) enabling the second part to be connected with the first part while the pin portion of the latter is in its safety position in a manual mode position wherein the first part is in rearward motion transmitting relation to the second part and (2) enabling the second part to be removed from the manual mode position while the pin portion of the first part is retained in its safety position. The second part includes a cap portion of a size and shape to be conveniently manually grasped by a user and moved rearwardly with respect to the housing assembly in order to effect the removal of the pin portion from its safety position when the second part is in its manual mode position.

Preferably the connection between the first and second parts includes oppositely facing locking surfaces integral with both parts. The cap member preferably includes an axial opening through which a rear end face of the removal portion of the first part is exposed when the cap member is in its manual mode position. The locking means integral with one of the parts is movable laterally (1) in response to the movement of the cap member into its manual mode position by the application of a forwardly directed force on the exterior of the cap member while the first part is held in its safety position against forward movement and (2) in response to the movement of the cap member out of its manual mode position by the application of a forwardly directed force on the rear end surface of the removal portion with the first part in its safety position and an opposing rearwardly directed force on the exterior of the cap member.

Another object of the present invention is the provision of a dual mode automatic injector which is simple in construction, economic to manufacture and effective in operation.

These and other objects of the present invention will become more apparent during the course of the following detailed description and appended claims.

The invention can best be understood in conjunction with the accompanying drawings wherein illustrative embodiments are shown.

In the drawings:

FIG. 1 is a longitudinal sectional view of a dual mode automatic injector embodying the principles of the present invention showing one form of dual mode safety device;

FIG. 2 is an end view of the injector viewed from the safety device end thereof;

FIG. 3 is an enlarged fragmentary sectional view of the dual mode safety device and the adjacent portion of the injector;

Figure 4:
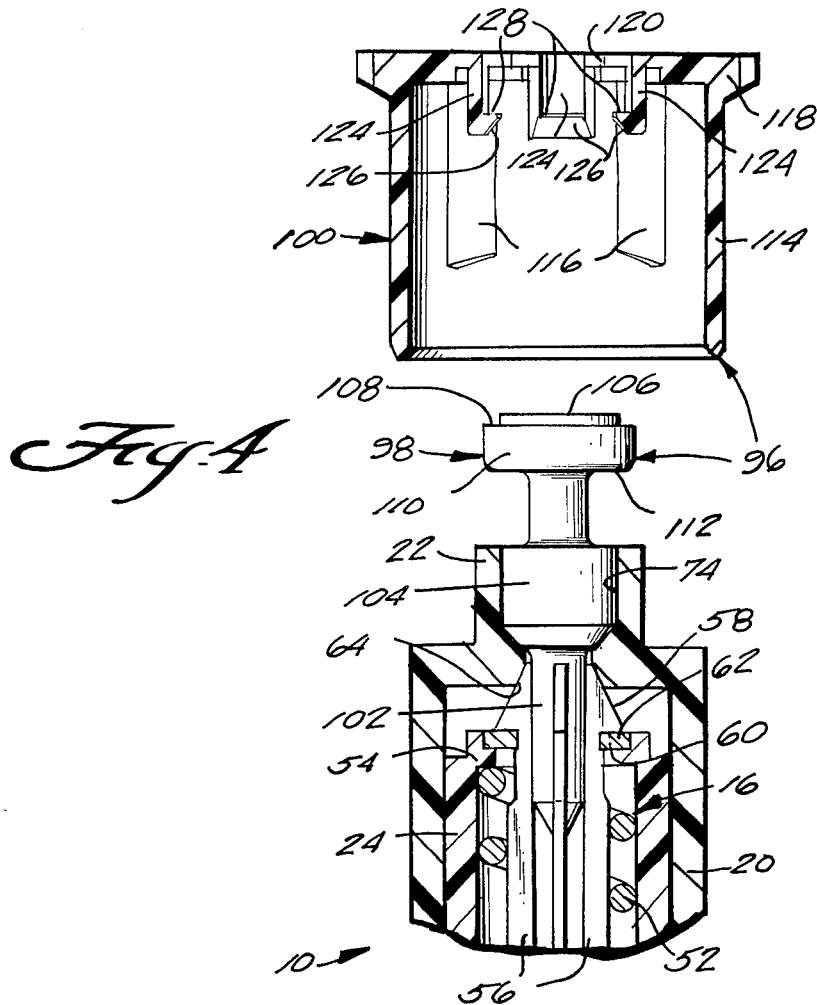
FIG. 4 is a view similar to FIG. 3 of another form of dual mode safety device embodying the principles of the present invention, showing the cap member of the device removed from its manual mode position.

Referring now more particularly to the drawings, there is shown in FIGS. 1–3 thereof a dual mode automatic injector, generally indicated at 10, embodying the principles of the present invention. The injector 10 includes a tubular housing assembly 12, a medicament injecting assembly, generally indicated at 14, within the forward end portion of the housing assembly 12, a stressed spring assembly, generally indicated at 16, within the rearward end portion of the housing assembly 12 in operative relation with the medicament injecting assembly 14 and a dual mode safety device, generally indicated at 18, at the rear of the housing assembly 12 in operative relation with the stressed spring assembly 16.

The housing assembly 12, medicament injecting assembly 14, and stressed spring assembly 16 are generally constructed in accordance with the teachings of U.S. Pat. No. 2,832,339, the disclosure of which is hereby incorporated by reference into the present specification. As best shown in FIG. 1, the housing assembly includes a cylindrical outer housing member 20 having a centrally apertured cylindrical rear wall portion 22 of reduced diameter on which the dual mode safety device 18 is mounted. The housing assembly 12 also includes an inner cylindrical housing member 24 within the housing member 20 within which is mounted the medicament injecting assembly 14 and the stressed spring assembly 16. The forward portion of the inner housing member 24 is formed with a counterbore for receiving therein a cylindrical dosage container 26. The forward end of the container is closed by a stopper or plug 28 of suitable rubber or plastic material. Plug 28 is retained in closing relation with the forward end of the container 26 by a housing end cap member 30 of molded plastic material. The cap is retained on the inner housing member 24 by interengagement of a pair of ridges 32 formed on the exterior periphery of the tubular member 24 with an annular groove 34 formed on the interior periphery of the cap member 30.

The rearward end of the dosage container 26 is closed by a plunger 36 which is slidably sealingly engaged within the rearward end thereof so as to enclose within the container a dosage 38 of a liquid medicament. A hypodermic needle 40 is disposed within the container 26 and has its pointed end disposed within a recess formed in the plug 28. A disk 42 of plastic is disposed within the forward end of the container 26 in surrounding sealed relation with the hypodermic needle 40 and in abutting engagement with the plug 28. The disk serves to releasably hold the needle in its storage position and to provide peripheral sealing therefor during the dosage injecting stroke of the plunger 36. The opposite end of the hypodermic needle 40 is enlarged for engagement by the plunger and has a slot formed in its periphery adjacent the enlarged end for communicating the dosage 38 with with the hollow interior of the hypodermic needle 40 when the plunger 36 is in engagement therewith. The inner housing member 24 is mounted within the outer housing member 20 for limited reciprocating movement as determined by a pair of ridges 46 formed on the exterior periphery of the tubular inner housing member 24 at a position spaced rearwardly from the pair of ridges 32. The pair of ridges 46 is adapted to engage within an elongated annular groove 48 formed on the interior periphery of the outer housing member 20.

The stressed spring assembly 16 includes an elongated callet member 50 made up of two interfitted stampings. The callet member is disposed within the rearward end portion of the housing member 24 and has its forward end disposed in abutment with the plunger 36. The forward end of the callet member 50 is also exteriorly configured to engage the forward end of a stressed coil spring 52 which surrounds the central portion of the elongated member 50 within the inner housing member 24 and has its rearward end engaged with an apertured end wall formed integrally on the rearward end of the inner housing member 24.

The rearward ends of the stampings of the elongated member 50 are split to provide four laterally movable spring fingers 56, the rearward extremities of which are formed with rearwardly and outwardly facing cam releasing surfaces 58. Extending inwardly from the forward end of each cam surface 58 is a locking shoulder 60 adapted to engage a locking ring 62 seated on the rear surface of the centrally apertured rear wall 54. The forward portion of the apertured cylindrical rear wall portion 22 is formed with a frusto-conical surface 64 which is disposed in engagement with the cam surfaces 58 so as to effect a laterally inward movement of the spring fingers toward one another to disengage locking shoulders 60 from locking ring 62 in response to a relative forward actuating movement of the outer housing member 20 with respect to the inner housing member 24.

The dual mode safety device 18 is made up of two separate cooperating parts, generally indicated at 66 and 68. The first part 66 is in the form of a safety pin member having a forward safety pin portion 70 of a size to enter through the apertured end wall portion 22 of the outer housing member 20 and into the apertured end wall 54 between the spring fingers 56. When the forward pin portion 70 is between the spring fingers 56, it is in a safety position which prevents the spring fingers 56 from moving laterally inwardly. The stressed spring assembly 16 is therefore prevented from being released.

As shown, the first part 66 includes an enlarged central portion 72 which is adapted to seat within a counterbored rear end 74 of the rear wall portion 20 when the forward safety pin portion 70 is in its safety position. Spaced rearwardly from the central portion 72 is a rearward removal portion which is defined (1) rearwardly by a rearward end surface 76, (2) peripherally by a relatively long rearward frusto-conical entry and abutment surface 78 which converges rearwardly and a relatively short forward annular locking surface 80 which faces forwardly and outwardly and (3) forwardly by a forwardly facing annular suface 82.

The second safety device part 68 is in the form of a cap member including a skirt portion 84 of a size to engage over the exterior of the outer housing member 20. Formed on the interior of the skirt portion 84 is a plurality of annularly spaced centering lug portions 86 the inner surfaces of which are shaped to engage the exterior periphery of the rear wall portion 22 of the outer housing member 20. The cap member part 68 also includes a radially outwardly extending gripping flange 88 in the rearward end thereof. An opening 90 is formed axially therein which is defined by a forward laterally deformable locking portion providing a rearwardly facing annular locking surface 92. A frusto-conical abutment surface 94 which converges rearwardly from the locking surface 92 defines the remainder of the opening 90.

FIGS. 1 and 3 of the drawings illustrate the condition of the dual mode safety device 18 when used in a single mode. In this mode, the cap member part 68 is releasably locked with the safety pin part 66 by holding the outer housing member 20 against forward movement with the safety pin part 66 in its safety position and then moving the cap member part 68 forwardly so that the entry and abutment surface 78 of the removable portion of the safety pin member 66 engages and deforms laterally the portion of the cap member defining the forward end of the opening 90. Continued forward movement of the cap member 68 serves to move abutment surface 94 into engagement with the entry and abutment surface 78, at which point locking surfaces 80 and 90 become interengaged. It will also be noted that during the aforesaid movement the skirt portion 84 of the cap member moves forwardly in surrounding relation to the rearward exterior periphery of the outer housing member 20 and the lug portions 86 engage the exterior periphery of the rear wall portion 22.

In the single unit mode, removal of the dual mode safety device 18 from the injector constitutes the first step in the use of the injector 10. This removal is accomplished simply by gripping the exterior periphery of the cap member part 68 and moving it rearwardly while gripping and holding the outer housing member 20. The removal of the cap member part 68 rearwardly carries with it the safety pin part 66 by virtue of the interengagement of the locking surfaces 80 and 92. With the safety pin portion 70 removed from its safety position which normally prevents the laterally inward movement of the spring fingers 56, the user can now complete the operation by moving the forward cap member 30 into contact with the thigh. By applying a continued forward force on the exterior periphery of the outer housing member 20, cam surfaces 64 thereof are moved forwardly with respect to the locking ring 62. This forward movement in cooperation with the cam surfaces 58 on the spring fingers 56 causes the locking surfaces 60 of the latter to move laterally inwardly of the locking ring 62 thus releasing the stressed spring 52. The spring 52 acts through the member 50 to move the same forwardly which has the effect of moving the plunger 36 with it. As the plunger moves forwardly, it carries with it the needle 40, the pointed forward end of which pierces through the plug 28 and into the muscle tissue of the thigh. At the same time, the dosage 38 of liquid medicament (atropine) within the container 26 is caused to move inwardly into the slot 44 of the needle and outwardly of the pointed forward end thereof as the same moves into the muscle tissue of the user. After the forward movement of the plunger has been completed, the user simply withdraws the needle 40 rearwardly.

As previously indicated, the other mode of use of the dual mode safety device 18 and injector 10 is a plural dosage mode in conjunction with pralidoxime chloride injector components. This mode is disclosed in the aforesaid commonly assigned concurrently filed application entitled "Plural Dosage Automatic Injector with Improved Safety", the disclosure of which is hereby incorporated by reference into the present specification. In the plural dosage mode, the cap member part 68 is separated and removed from the safety pin part 66. This removal is accomplished by applying a forwardly directed force on the rearward end surface 76 of the safety pin part 66 so as to retain the safety pin portion 70 in its safety position and by simultaneously applying an opposing rearwardly directed force on the exterior of the cap member part 68. The application of these opposing forces has the effect of releasably disengaging the locking surfaces 80 and 92. It will be understood that the portion of the cap member defining the forward end of the opening 90 will deform laterally to permit the cap member to pass beyond the entry and abutment surface 78 of the safety pin part 66. In this way the cap member part 68 is removed from the safety pin part 66 while the latter is retained in its 20 safety position.

In accordance with the disclosure contained in the aforesaid application, a slotted tubular actuating member is fitted to the rear wall portion 22 and mounted within the dual dosage injector housing assembly which provides a fixed holding member which extends through the slot in the tubular actuating member in a position forwardly of the surface 82 of the safety pin part 66. As the actuating member is advanced forwardly, the holding member prevents the safety pin part 66 from moving forwardly with the outer housing 20. After the housing member 20 has been moved forwardly by the actuating member a distance sufficient to remove the safety pin portion 70 from its safety position between the spring fingers 56, the forward movement of the inner housing member 24 is arrested so that the last portion of the forward movement of the outer housing member 20 has the effect of releasing the stressed spring assembly 16 as aforesaid.

Figure 5:
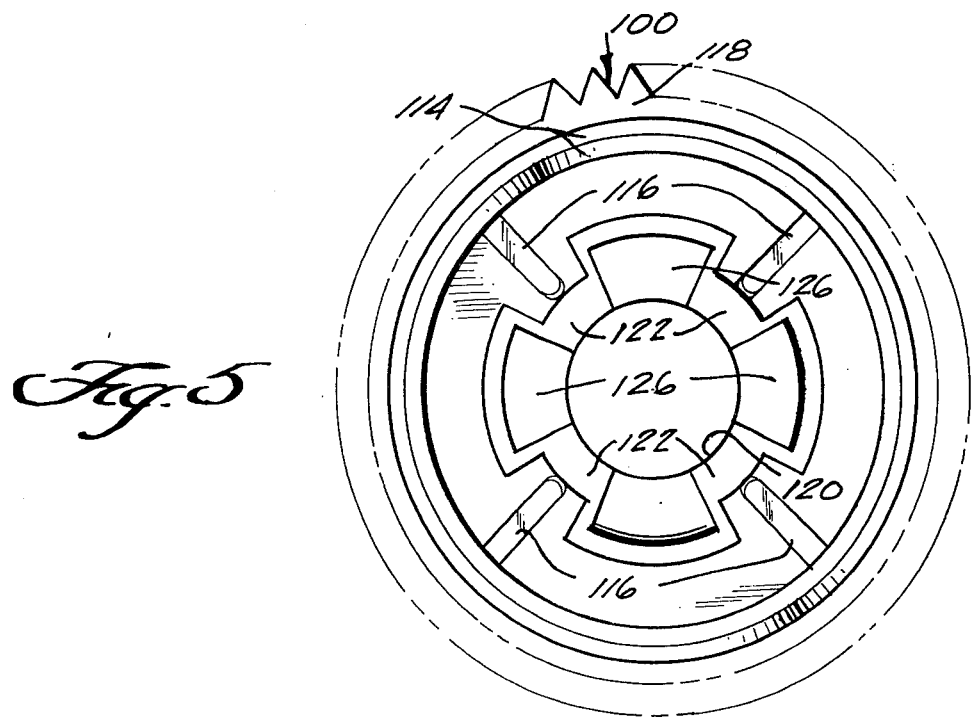
FIG. 5 is a front end view of the cap member shown in FIG. 4.

Referring now more particularly to FIGS. 4 and 5 of the drawings, there is shown therein a dual mode safety device 96, of modified construction which embodies the principles of the present invention and can be utilized in the injector 10 in lieu of the safety device 18. As with the device 18, the dual mode safety device 96 is made up of two separate cooperating parts, generally indicated at 98 and 100. As before, the first part 98 is in the form of a safety pin member having a forward safety pin portion 102 of a size to enter through the apertured end wall portion 22 of the outer housing member 20 and into the apertured end wall 54 between the spring fingers 56.

The safety pin part 98 also includes an enlarged central portion 104 which is adapted to seat within the counterbored rear end 74 of the rear wall portion 20 when the forward safety pin portion 102 is in its safety position. Spaced rearwardly from the central portion 104 is a rearward removal portion which includes a circular rear end surface 106 peripherally recessed and a recessed rearwardly facing abutment surface 108 surrounding the rear surface 106. A cylindrical peripheral surface 110 extends forwardly from the surface 108 and a forwardly facing annular surface 112 extends radially inwardly from the forward end of surface 110.

The second safety device part 100 is in the form of a cap member including a skirt portion 114 of a size to engage over the exterior of the outer housing member 20. Formed on the interior of the skirt portion 114 is a plurality of annularly spaced centering rib portions 116 the inner surfaces of which are shaped to engage the exterior periphery of the rear wall portion 22 of the outer housing member 20. The cap member part 100 also includes a radially outwardly extending gripping flange 118 in the rearward end thereof. An opening 120 is formed axially therein in the form of a circle having four annularly spaced segmental notches formed in the periphery thereof. The portions defined by the notches have forwardly facing abutment surfaces 122. Extending forwardly between the abutment surfaces 122 in alignment with the notches of the opening 120 is a plurality of annularly spaced spring fingers 124, the forward ends of which define rearwardly and inwardly inclined entry surfaces 126 leading rearwardly to radially outwardly extending locking surfaces 128 which face rearwardly. The cap member part 100, is releasably locked with the safety pin part 98 by holding the outer housing member 20 against forward movement with the safety pin part 98 in its safety position as shown in FIG. 4 and then moving the cap member part 100 from the position shown forwardly so that the rearward edge of the cylindrical surface 110 of the removable portion of the safety pin member 98 engages the entry surfaces 126 and deforms laterally the spring fingers 124 of the cap member 100. Continued forward movement of the cap member 100 serves to effect a relative movement of the forward edge of cylindrical surface 110 passed the entry surfaces 126, at which point locking surfaces 128 become interengaged with the forward annular surface 112. It will also be noted that during the aforesaid movement the skirt portion 114 of the cap member moves forwardly in surrounding relation to the rearward exterior periphery of the outer housing member 20 and the rib portion 116 engage the exterior periphery of the rear wall portion 22.

In the single unit mode with cap member part 100 releasably locked to the safety pin part 98 as aforesaid, removal of the dual mode safety device 96 from the injector constitutes the first step in the use of the injector 10. As before, this removal is accomplished simply by gripping the exterior periphery of the cap member part 100 and moving it rearwardly while gripping and holding the outer housing member 20. The removal of the cap member part 68 rearwardly carries with it the safety, pin part 66 by virtue of the interengagement of the locking surfaces with the annular surface 112. With the safety pin portion 102 removed from its safety position which normally prevents the laterally inward movement of the spring fingers 56, the user can now complete the operation of the injector 10 in the manner previously described.

As before, in the plural dosage mode, the cap member part 100 is separated and removed from the safety pin part 98. This removal is accomplished by applying a forwardly directed force on the rearward end surface of the safety pin part 98 so as to retain the safety pin portion 102 in its safety position and by simultaneously applying an opposing rearwardly directed force on the exterior of the cap member part 100. The application of these opposing forces has the effect of releasably disengaging the locking surfaces 128 from the annular surface 112. It will be understood that the spring fingers 124 of the cap member will deform laterally to permit the cap member to pass beyond the cylindrical surface 110 of the safety pin part 97. In this way the cap member part 100 is removed from the safety pin part 66 while the latter is retained in its safety position. The dual mode operation is the same as that previously described.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed:

1. In a spring actuated injector comprising an elongated tubular housing assembly having a forward end adapted to engage a patient and a centrally apertured rear wall, a medicament injecting assembly within the forward end portion of said housing assembly, said medicament injecting assembly including a container, a hypodermic needle, a liquid medicament and a plunger, a stressed spring assembly in the rearward end portion of said housing assembly disposed in operative relation with said medicament injecting assembly for operating the latter so as to move the plunger forwardly within the container, the needle forwardly into a patient, and the liquid medicament outwardly of the needle, said stressed spring assembly including releasable means operable in response to a manual actuating procedure which included the application of a forwardly directed force on said housing assembly while the forward end thereof is in engagement with the patient to release said stressed spring assembly to operate said medicament injection assembly, the improvement which comprises dual mode safety means for preventing the release of said releasable means except when it is desired to operate said medicament injecting assembly, said dual mode safety means including a first part including pin means disposed in safety position extending through the central aperture in said rear wall in release preventing relation with said releasable means for removal therefrom in response to a relative rearward movement with respect to said rear wall so as to permit an actuating movement to release said releasable means, said first part including an automatic mode portion fixed to the rearward end of said pin portion, said automatic mode portion being of a size greater than said pin means but less than said rear wall so as to present a forwardly facing surface spaced rearwardly from said rear wall operable to be engaged by a holding member of an automatic actuating system while a moving member of such system is moved forwardly into engagement with the rear wall to provide both a relative rearward removal movement for said pin means and an actuating movement for said releasable means, said dual mode safety means including a separate second part and connecting means acting between said first and second parts for (1) enabling said second part to be connected with said first part while the pin means of the latter is in said safety position in a manual mode position wherein said first part is in rearward motion transmitting relation to said second part and (2) enabling said second part to be removed from said manual mode position while the pin means of said first part is retained in said safety position, Said second part including a manual mode cap member of a size and shape to be conveniently manually grasped by a user and moved rearwardly with respect to said housing assembly in order to effect the removal of the pin means from said safety position when said second part is in manual mode position.

2. The improvement as defined in claim 1 wherein said connecting means includes rearwardly facing locking means integral with the cap member of said second part and forwardly facing locking means integral with the automatic mode portion of said first part engagable with said rearwardly facing locking means when said cap member is in said manual mode position.

3. The improvement as defined in claim 2 wherein said cap member includes an opening extending therethrough and said automatic mode portion includes a rear end surface exposed rearwardly through said opening when said cap member is in said manual mode position.

4. The improvement as defined in claim 3 wherein the locking means integral with one of said parts is movable laterally, (1) in response to the movement of said cap member into its manual mode position by the application of a forwardly directed force on the exterior of said cap member while said first part is held in its safety position against forward movement and (2) in response to the movement of said cap member out of its manual mode position by the application of a forwardly directed force on the rear end surface of said automatic mode portion with said first part in said safety position and an opposing rearwardly directed force on the exterior of said cap member.

5. The improvement as defined in claim 4 wherein the movable means is integral with said cap member and constitutes an integral annular portion at the forward end of said axial opening.

6. The improvement as defined in claim 4 wherein said movable locking means is integral with said cap member and comprises a plurality of spring fingers disposed in annularly spaced relation about the forward end of said axial opening.

7. The improvement as defined in claim 4 wherein said cap member includes a forwardly facing abutment surface and said automatic mode portion includes a rearwardly facing abutment surface for engaging said forwardly facing abutment surface when said cap member is in said manual mode position.

8. The improvement as defined in claim 4 wherein said cap member includes an exterior peripheral flange entending radially outwardly from the rearward end thereof.

* * * * *